United States Patent
Summers et al.

(10) Patent No.: US 7,247,650 B2
(45) Date of Patent: Jul. 24, 2007

(54) MACROLIDES AND METHODS FOR PRODUCING SAME

(75) Inventors: Mia Haruna Yoshino Summers, Nyack, NY (US); Edmund Idris Graziani, Ridgewood, NJ (US); Margaret M. Leighton, Suffern, NY (US); Kevin Pong, Robbinsville, NJ (US); Roger Alan Kele, Guilford, CT (US); David P. Labeda, Dunlap, IL (US)

(73) Assignee: Wyeth, Madison, NJ (US)

( * ) Notice: Subject to any disclaimer, the term of this patent is extended or adjusted under 35 U.S.C. 154(b) by 191 days.

(21) Appl. No.: 11/065,934

(22) Filed: Feb. 25, 2005

(65) Prior Publication Data

US 2005/0197379 A1    Sep. 8, 2005

Related U.S. Application Data

(60) Provisional application No. 60/549,480, filed on Mar. 2, 2004.

(51) Int. Cl.
C07D 498/18  (2006.01)
A61K 31/407  (2006.01)

(52) U.S. Cl. .................... 514/411; 540/456
(58) Field of Classification Search ............ 540/456; 514/411
See application file for complete search history.

(56) References Cited

U.S. PATENT DOCUMENTS

| 5,508,398 A | 4/1996 | Gletos et al. |
| 6,500,843 B2 | 12/2002 | Steiner et al. |
| 2002/0052372 A1 | 5/2002 | Steiner et al. |

FOREIGN PATENT DOCUMENTS

| EP | 0 378 321 A2 | 7/1990 |
| EP | 0 528 452 A | 2/1993 |
| EP | 0 528 452 A1 | 2/1993 |
| WO | WO 94/18207 | 8/1994 |
| WO | WO 00/10553 A2 | 3/2000 |

OTHER PUBLICATIONS

Salituro et al, Meridamycin: A Novel Nonimmunosuppressive FKBP12 Ligand From Streptomyces Hygroscopicus, Tetrahedron Letters, vol. 36, No. 7, pp. 997-1000, (Feb. 13, 1995).

Snyder et al, Immunophilins in the Nervous System, Neuron, vol. 21, No. 2, pp. 283-294, (Aug. 1998).

Hamilton et al, Immunophilin Ligands for the Treatment of Neurological Disorders, Expert Opinion on Therapeutic Patents, vol. 8, No. 9, pp. 1109-1124, (1998).

Herdegen et al, Immunophilin Ligands as a Novel Treatment for Neurological Disorders, Trends in Pharmacological Sciences, Elsevier Trends Journal, vol. 21, No. 1, pp. 3-5, (Jan. 2000).

Snyder et al, Immunophilins and the Nervous System, Nature Medicine, vol. 1, No. 1, pp. 32-37, (Jan. 2000).

Constantini et al, A Novel Immunophilin Ligand: Distinct Branching Effects on Dopaminergic Neurons in Culture and Neurotrophic Actions After Oral Administration in an Animal Model of Parkinson's Disease, Neurobiology of Disease, vol. 5, No. 2, pp. 97-106, (Apr. 1998).

Gold, FK506 and The Role of Immunophilins in Nerve Regeneration, Molecular Neurobiology, vol. 15, No. 3, pp. 285-306, (Dec. 1997) Abstract.

Constantini et al, Immunophilin Ligands can Prevent Progressive Dopaminergic Degeneration in Animal Models of Parkinson's Disease, European Journal of Neuroscience, vol. 13, No. 6, pp. 1085-1092, (Mar. 2001).

Snyder et al, Neural Actions of Immunophilins Ligands, Trends in Pharmacological Sciences, vol. 19, No. 1, (Jan. 1998) Abstract.

Bierer et al, Probing Immunosupppressant Action with a Nonnatural Immunophilin Ligand, Science, American Association for the Advancement of Science, vol. 250, No. 4980, pp. 556-559, (Oct. 26, 1990).

Mia Y. Summers, et al., "3-Normeridamycin: A Potent Non-Immunosuppressive Immunophilin Ligand is Neuroprotective in Dopaminergic Neurons", J. Antibiotic. 59(3): 184-189 (Mar. 2006).

Pong et al, Attenuation of Staurosporine-Induced Apoptosis, Oxidative Stress, and Mitochondrial Dysfunction by Synthetic Syperoxide Dismutase and Catalase Mimetics, in Cultured Cortical Neurons, Experimenal Neurology, 171, pp. 84-97, (Sep. 2001).

Prochiantz et al, Specific Stimulation of in vitro Maturation of Mesencephalic Dopaminergic Neurones by Striatal Membranes, Nature vol. 293, pp. 570-572, (Oct. 15, 1981).

Wood et al, Stimulation of Neurite Outgrowth by Immunophilin Ligands: Quantitative Analysis by Cellomics Arrayscan, Abstract, Program No. 104.3; Society for Neuroscience (2004), www.sfn.scholarone.com.

*Primary Examiner*—Bruck Kifle
(74) *Attorney, Agent, or Firm*—Arnold S. Milowsky; Howson & Howson LLP

(57) ABSTRACT

This invention relates, in part, to macrolide compounds, actinomycete strains for producing them, and pharmaceutical compositions containing them.

3 Claims, 1 Drawing Sheet

MACROLIDES AND METHODS FOR PRODUCING SAME

CROSS-REFERENCE TO RELATED APPLICATIONS

This is an application claiming the benefit under 35 USC 119(e) of U.S. Provisional Patent Application No. 60/549,480, filed Mar. 2, 2004.

BACKGROUND OF THE INVENTION

In one aspect, this invention relates to neuroprotective and neuroregenerative compositions and derivatives and analogs thereof. More specifically, the invention relates to actinomycete strains for production of the neuroprotective and neuroregenerative compositions, pharmaceutical compositions containing the neuroprotective and neuroregenerative compositions and analogs, methods of making the neuroprotective and neuroregenerative compositions and methods of use thereof.

Immunophilins are proteins found in the immune systems and nervous systems of various cell types, e.g., bacteria, yeast, and a number of different types of mammalian cells. Classes of immunophilins include cyclophilins and FK506-binding proteins (e.g., FKBPs). Cyclosporin A is a macrolide immunophilin ligand that binds to cyclophilins. Other macrolide immunophilin ligands, such as meridamycin, FK506, and rapamycin, are understood to bind to FKBPs.

One way to describe intracellular functions of immunophilins is by identification of their enzymatic activity. Functions of FKBPs, for example, can be described in terms of their rotamase (i.e., petidy-prolyl cis-trans isomerase) activity.

FK506 and rapamycin are immunosuppressive immunophilin ligands. Meridamycin, on the other hand, is non-immunosuppressive. Salituro, et al., *Tetrahedron Letters*, Vol. 36, No. 7, 997–1000 (1995). In fact, meridamycin is an antagonist of both FK506 and rapamycin. (WO 94/18207).

Other non-immunosuppressive immunophilins are described by Steiner et al. (U.S. Pat. No. 6,500,843) who discuss using neurotrophic pipecolic acid derivative compounds having an affinity for FKBP-type immunophilins as inhibitors of the enzyme activity associated with immunophilin proteins, and particularly inhibitors of peptidyl-prolyl isomerase or rotamase enzyme activity to stimulate or promote neuronal growth or regeneration.

Meridamycin has been identified for uses such as an antidote for an overdose of macrophilin-binding-immunosuppressants such as FK506 or rapamycin, a steroid potentiator, and/or an anti-infective agent for infections or infectious diseases caused by organisms producing MIP (macrophage infectivity potentiator) or Mip-like factors. (WO 94/18207). In addition, meridamycin may be useful in the treatment of inflammatory/hyperproliferative skin diseases. (WO 94/18207).

It is desirable to find compounds that are neurotrophic, e.g., neuroprotective and/or neuroregenerative. A need exists in the art to provide compounds, and therapeutic drugs comprising such compounds.

SUMMARY OF THE INVENTION

In one aspect, the present invention relates to compounds of formula (I)

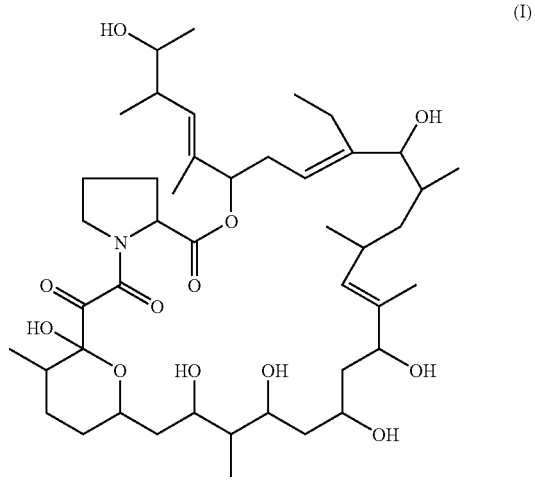

or pharmaceutically acceptable salts thereof. The invention is useful in preparation of compositions, including medicaments, further comprising one or more pharmaceutically acceptable carriers, excipients, or diluents.

In another aspect, the invention provides novel actinomycete strains LL-C31037 and BD240 which can be cultured under conditions which permit them to produce macrolides and other chemical compounds produced. Fermentation of actinomycete strains LL-C31037 and BD240, for example, can be used to produce novel compounds having formula (I), as well as meridamycin (formula (II)).

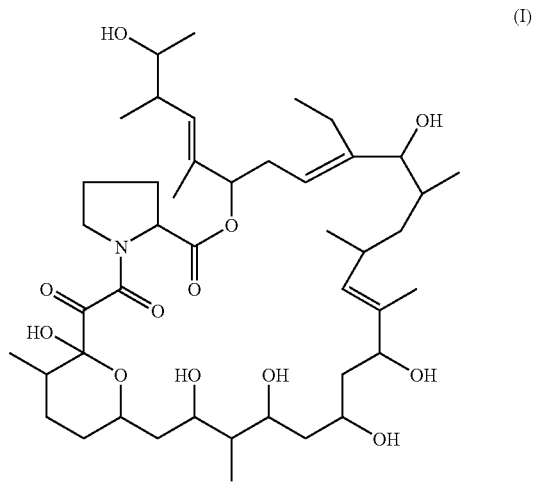

-continued

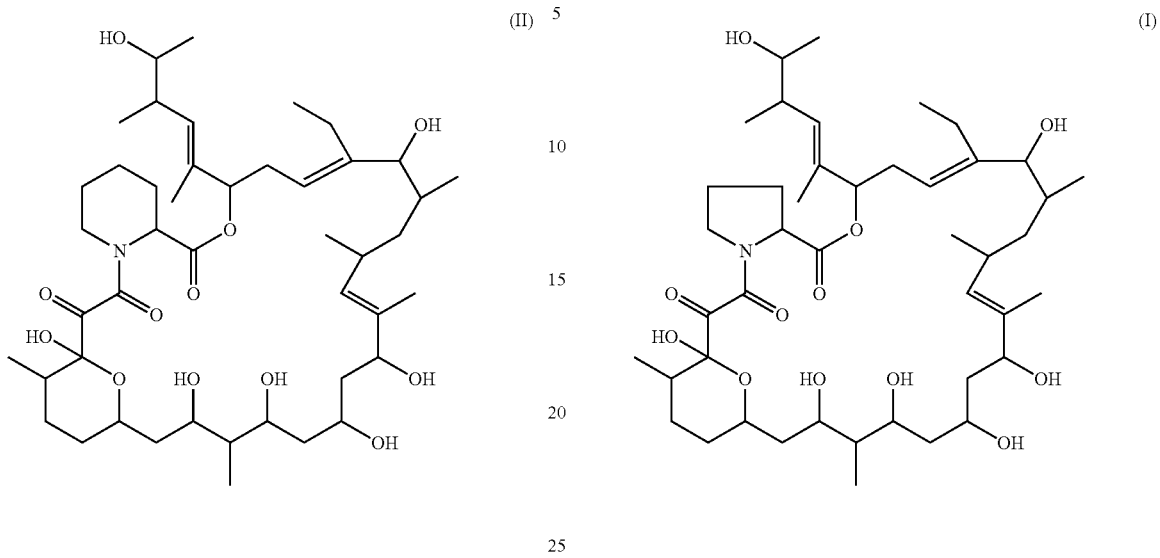

In yet another aspect, the invention provides methods of isolating purified compounds of formula (I) and formula (II) from cultures of the novel actinomycete strains LL-C31037 and BD240 of the invention. The invention further provides pharmaceutical compositions containing the compounds produced by the novel strains of the invention.

In a further aspect, the invention provides methods for treating a mammal comprising administering to the mammal a compound or composition of the invention, particularly for treatment of a neurological disorder.

Still other aspects and advantages of the invention will be readily apparent from the following detailed description of the invention.

DETAILED DESCRIPTION OF INVENTION

Figure 1:
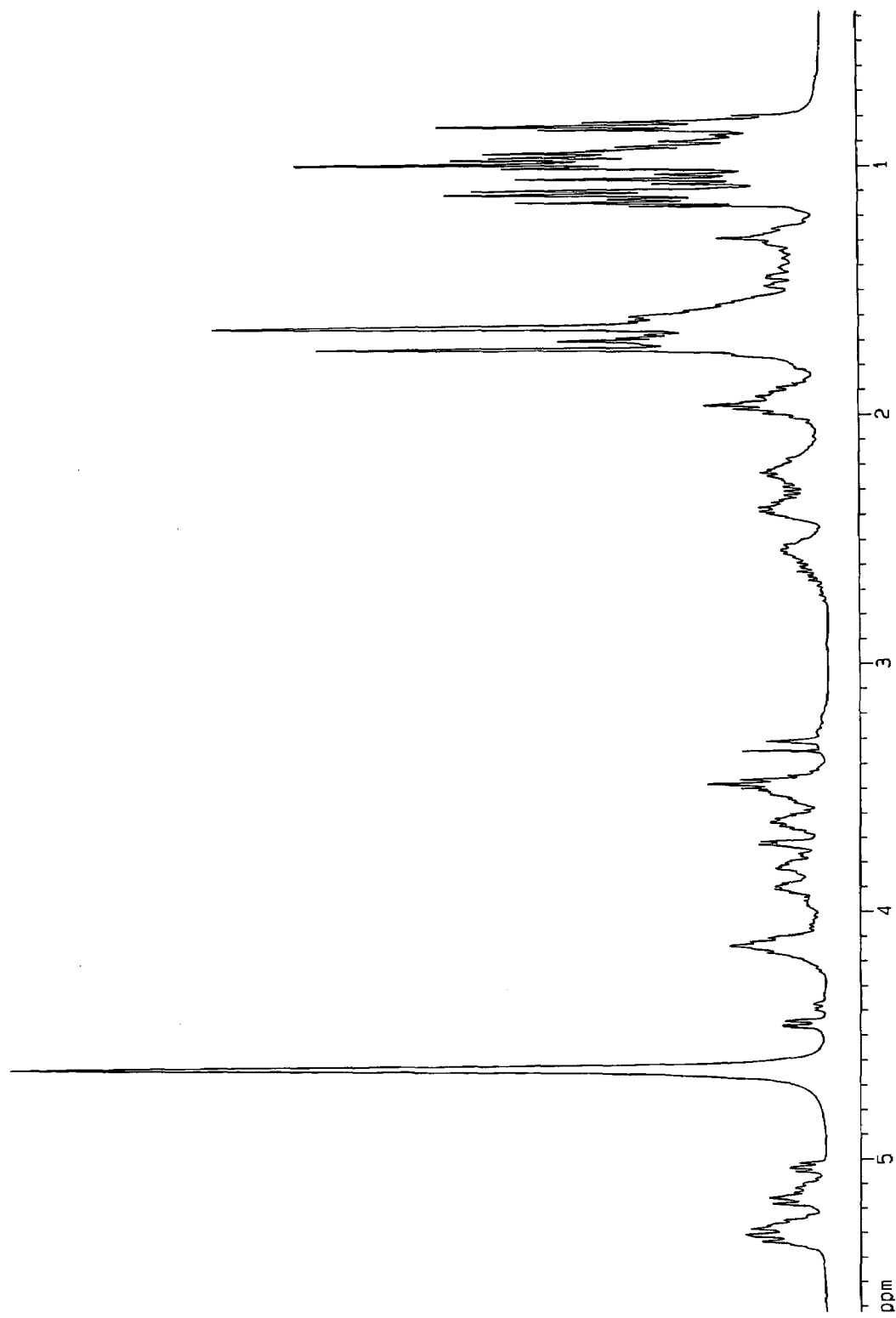
FIG. 1 is a proton nuclear magnetic resonance (NMR) spectrum of the compound of formula (I) in CD$_3$OD at 400 mHz.

The invention relates, in part, to macrolide compounds, neuroprotective and neuroregenerative compositions containing them, and actinomycete strains for production of the compounds. The invention further relates to methods of producing the compounds in the actinomycete strains.

More particularly, the invention provides a compound of formula (I), or a pharmaceutically acceptable salt thereof.

The terms "pharmaceutically acceptable salts" and "pharmaceutically acceptable salt" refer to salts derived from organic and inorganic acids such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

While shown without respect to stereochemistry in formula (I) and (II), the compounds of formula (I) or (II) can contain one or more chiral centers. Reference to "compound of formula (I)" or "compound of formula (II)" is understood to include any compound of the implicated structural formula including all stereoisomers thereof.

The physicochemical characteristics of the compound of formula (I) are as follows:

Apparent Molecular Formula: $C_{44}H_{73}NO_{12}$

Molecular Weight: Positive Ion Electrospray m/z=830.9 (M+Na)$^+$; Negative Ion Electrospray MS m/z=807.4 (M−H)$^-$; High Resolution Fourier Transform MS m/z=830.50021 (M+Na)$^+$.

Ultraviolet Absorption Spectrum: $\lambda_{max}$ nm (acetonitrile/water)=210 nm, end absorption.

Optical Rotation $[\alpha]^{25}_D$ −1.1 (c 1.0, MeOH)

Proton Magnetic Resonance Spectrum: (400 MHz CD$_3$OD): See, e.g., FIG. 1.

For the production of the neuroprotective compound (I) the present invention is not limited to a particular organism, for example, Streptomyces species designated LL-C31037 and BD240. In fact, it is desired and intended to include the use of naturally-occurring mutants of this organism, as well as induced mutants produced from this organism by various mutagenic means known to those skilled in the art, for example, exposure to nitrogen mustard, X-ray radiation, ultraviolet radiation, N'-methyl-N'-nitro-N-nitrosoguanidine, or actinophages. It is also desired and intended to include inter- and intraspecific genetic recombinants produced by genetic techniques known to those skilled in the art such as, for example, conjugation, transduction and genetic engineering techniques.

In one embodiment, compounds and methods of producing the compounds relate to isolates (cells) of actinomycete strains that are classified in the genus Streptomyces by 16S rDNA sequence comparison. The isolates of the actinomycete strains produce no aerial mycelium and tan mycelium with no soluble pigment when grown on agar medium, e.g., ATCC agar medium as described herein, No. 172 or 174 (ATCC Media Handbook, $1^{st}$ edition, 1984). Alternatively, other suitable media may be purchased commercially, e.g., Sigma (St. Louis, Mo.). In a further embodiment, the isolates of the actinomycete strains produce at least one compound which is a compound of Formula I or a compound of Formula II. In a further embodiment the isolates of the actinomycete strains produce both a compound of Formula I and a compound of Formula II.

Additional disclosure relating to compounds of formula (II) and use thereof is provided in commonly assigned U.S. Provisional Application entitled "Non-Immunosuppressive Immunophilin Ligands As Neuroprotective And/Or Neuroregenerative Agents" bearing attorney docket AM101605/WYNC-0803, U.S. patent application Ser. No. 60/569,430 filed Mar. 2, 2004.

The methods preferably involve growth in fermentation of the actinomycete strains LL-C31037 and BD240. In another embodiment, methods are provided that involve culturing actinomycete strains under suitable conditions to produce the compounds having formulas (I) and/or (II).

In one embodiment, the invention provides actinomycete strain LL-C31037, which was deposited pursuant to the provisions of the Budapest Treaty with the Agricultural Research Service Culture Collection (NRRL), 1815 North University Avenue, Peoria, Ill. 61604, on Mar. 1, 2004 and assigned the NRRL designation number 30721. In another embodiment, the invention provides actinomycete strain BD240, which was deposited pursuant to the provisions of the Budapest Treaty with the Agricultural Research Service Culture Collection (NRRL), 1815 North University Avenue, Peoria, Ill. 61604, on Jan. 19, 2005, and assigned the NRRL designation number 30810. The invention further provides isolates of the novel strains of the invention and derivatives, mutants, recombinants, and modified forms thereof which are characterized by the ability to produce a compound of formula (I) and/or formula (II). In one embodiment, the derivatives, mutants, recombinants, and modified forms thereof are further characterized by one or more of the following characteristics: not producing aerial mycelium, producing substrate mycelium which is tan and producing no soluble pigment.

Fermentation conditions to culture Streptomyces species LL-C31037 and BD240 for production of macrolide compounds including the novel compound (I) and/or compound (II) can be performed in flasks. Alternatively, production of higher volumes can be performed in fermentors under similar conditions.

Media useful for the cultivation of Streptomyces sp. LL-C31037 and BD240 and the production of the macrolide compounds include assimilable carbon sources such as, for example, dextrose, sucrose, glycerol, molasses, starch galactose, fructose, corn starch, malt extract and combinations thereof; an assimilable source of nitrogen such as, for example, ammonium chloride, ammonium sulfate, ammonium nitrate, sodium nitrate, amino acids, protein hydrolysates, corn steep liquor, casamino acid, yeast extract, peptone, tryptone and combinations thereof; and inorganic anions and cations such as, for example, potassium, sodium, sulfate, calcium, magnesium, chloride. Trace elements such as, for example, zinc, cobalt, iron, boron, molybdenum, and copper are supplied as impurities of other constituents of the media. Aeration in tanks and bottles is supplied by forcing sterile air through or onto the surface of the fermenting medium. A mechanical impeller provides further agitation in tanks. An antifoam agent such as polypropylene glycol can be added as needed.

Fermentation conditions for cultivation under controlled conditions of an actinomycete strain such as described herein, to produce a neuroprotective and neuroregenerative compound of formula (I) in growth media.

In one embodiment, a fermentation production medium is prepared by combining dextrose in a weight percentage of about 1% to about 2%; about 1% to about 3% of a soy source, about 0.25% to about 1% of yeast, about 0.1% of a calcium source, about 5% to about 10%, and preferably 6% to 8% maltodextrin, and, optionally, proline, from 0 to 0.5%. Optionally, other components may be included. Suitably, the media is adjusted to a pH in the range of about 6.5 to 7.5, and preferably about 6.8 to 7. Typically, the culture is allowed to ferment with suitable agitation and aeration. Alternatively, other suitable fermentation media may be prepared by one of skill in the art substituting other appropriate carbon source or other components and/or purchased commercially. See, generally, e.g., Sigma Aldrich (St. Louis, Mo.); G. J. Tortora et al, Microbiology: An Introduction Media Update (Benjamin Cummings Publishing Co; Oct. 1, 2001); Maintaining Cultures for Biotechnology and Industry, eds. J. C. Hunter-Cevera and A. Bet (Academic Press, Jan. 25, 1996).

After about 5 to 10 days, and preferably about 7 days of fermentation, the cells from the culture are pelleted by centrifugation. In one embodiment, the cells are extracted with a suitable solvent, e.g., ethyl acetate. The extract is concentrated in vacuo and resuspended in a minimum volume of a suitable solvent, e.g., methanol. The solution is loaded onto a reverse phase silica column and eluted with 20%–100% methanol in water. The fractions eluting from 60% methanol to 100% methanol are concentrated in vacuo. The prolylmeridamycin containing fractions are separated by suitable means, e.g., chromatographic methods.

In another embodiment, the supernatant is mixed with a suitable resin and allowed to rest from about 8 to 16 hours. Thereafter, the resin is washed with a suitable solvent, e.g., methanol, and the filtrate collected. To the cell pellet, an ethyl acetate—methanol mixture is added. This is repeatedly shaken and centrifuged, and the supernatant collected. The cell supernatant and the broth methanol filtrate are combined and concentrated in vacuo. Crude extract is adsorbed onto silica, and fractionated by vacuum liquid chromatography (VLC). The compound is eluted with a suitable solvent, e.g., methanol in dichloromethane. This extract is concentrated, adsorbed onto silica and loaded onto a flash silica column. The compound is eluted with a suitable solvent, concentrated and further purified by column chromatography.

The presence of the compound of formula I in the crude or semi-purified material can be confirmed by conventional methods, e.g., liquid chromatography mass spectrometric (LCMS) analysis of fractions. These fractions may be pooled and further purified by chromatographic methods, and optionally concentrated, e.g., in vacuo.

The resulting purified compounds are free of cells and cellular materials, by-products, reagents, and other foreign material as necessary to permit handling and formulating of the compound for laboratory and/or clinical purposes. It is preferable that purity of the compounds used in the present invention have a purity of greater than 80% by weight; more preferably at least 90% by weight, even more preferably greater than 95% by weight; yet even more preferably at least 99% by weight. In one embodiment, the invention provides compositions containing the compounds of the invention, regardless of how such compounds are produced.

Although not intending to be limited in its therapeutic applications, it is desirable to use a compound of formula (I) for treatment of conditions of the central nervous system, neurological disorders, and disorders of the peripheral nervous system. Conditions affecting the central nervous system include, but are not limited to, epilepsy, stroke, cerebral ischemia, cerebral palsy, multiple sclerosis, Alper's disease, Parkinson's disease, Alzheimer's disease, Huntington's disease, amyotrophic lateral sclerosis (ALS), dementia with Lewy bodies, Rhett syndrome, neuropathic pain, spinal cord trauma, or traumatic brain injury.

Neurological disorders according to the invention include, but are not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by lead, acrylamides, gamma-diketones (glue-sniffer's neuropathy), carbon disulfide, dapsone, ticks, porphyria, Gullain-Barre syndrome, dimentia, Alzheimer's disease, Parkinson's disease, and Huntington's chorea.

Specific situations in which neurotrophic therapy is indicated to be warranted include, but are not limited to, central nervous system disorders, Alzheimer's disease, aging, Parkinson's disease, Huntington's disease, multiple sclerosis, amyotrophic lateral sclerosis, traumatic brain injury, spinal cord injury, epilepsy, inflammatory disorders, rheumatoid arthritis, autoimmune diseases, respiratory distress, emphysema, psoriasis, adult respiratory distress syndrome, central nervous system trauma, and stroke.

The term "subject" or "patient," as used herein, refers to a mammal, which may be a human or a non-human animal.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The compounds of this invention are also useful in preventing, treating or inhibiting senile dementias, dementia with lewy bodies, mild cognitive impairment, Alzheimer's disease, cognitive decline, associated neurodegenerative disorders, as well as providing neuroprotection or cognition enhancement.

The terms "effective amount" and "therapeutically effective amount," as used herein, refer to the amount of a compound of formula (I) that, when administered to a patient, is effective to at least partially ameliorate a condition from which the patient is suspected to suffer.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual subject being treated. Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally.

Effective administration of the compounds of this invention may be given at monthly, weekly, or daily, or other suitable intervals. For example, a parenteral dose may be delivered on a weekly basis at a dose of about 10 mg to about 1000 mg, about 50 mg to about 500 mg, or about 100 mg to about 250 mg per week. A suitable oral dose may be greater than about 0.1 mg/day. Preferably, administration will be greater than about 10 mg/day, more specifically greater than about 50 mg/day in a single dose or in two or more divided doses. The oral dose generally will not exceed about 1,000 mg/day and more specifically will not exceed about 600 mg/day. The projected daily dosages are expected to vary with route of administration.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearyl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

The invention further provides products, including packaging, containing the compounds formulated for delivery. In another aspect, the invention provides kits including, e.g., needles, syringes, and other packaging, for delivery of the compound of the invention. Optionally, such a kit may include directions for administration of the drug, diluent, and or a carrier for mixing of a solid form of a compound of the invention.

The reagents used in the preparation of the compounds of this invention can be either commercially obtained or can be prepared by standard procedures described in the literature.

The preparation of representative examples of this invention are described in the following examples.

EXAMPLE 1

Fermentation Conditions for Actinomycete Strain LL-C31037

Fermentation conditions for cultivation under controlled conditions of an actinomycete strain designated LL-C31037 produce a neuroprotective and neuroregenerative compound of formula (I) in the growth media.

The actinomycete strain is maintained in the culture collection of Wyeth Research, Pearl River, N.Y. 10965, as culture LL-C31037. A viable culture of this microorganism has been deposited under the Budapest Treaty with the Patent Culture Collection, Northern Regional Research Laboratory (NRRL), U.S. Department of Agriculture, Peoria, Ill. 61604, and added to its permanent collection. Culture LL-C31037 has been assigned the NRRL accession number 30721, deposited on Mar. 1, 2004.

Culture of actinomycete strain LL-C31037 on agarplates, e.g., ATCC agar medium No. 172, produces no aerial mycelium. The substrate mycelium is tan and no soluble pigment is produced. The 16S rDNA sequence was determined for strain LL-C31037 following isolation and direct sequencing of the amplified gene. The nucleotide sequence was aligned with the sequences of previously studied streptomycetes, and phylogenetic trees were generated by using two neighbor-joining tree algorithms. The 16S rDNA sequence supported classification of the strain in the genus *Streptomyces*.

Fermentation conditions to culture *Streptomyces* species LL-C31037 for production of compound (I) were performed in flasks. Alternatively, production of higher volumes was performed in fermentors under similar conditions.

A. Flask Fermentation

A seed medium of the following formulation was be prepared by combining: dextrose (added after autoclaving), 1%; soluble starch, 2%; yeast extract, 0.5%; N-Z amine type A (Sheffield), 0.5%; calcium carbonate, 0.1%; pH at 7.0.

Ten ml of seed medium in a 25×150 mm glass tube was inoculated with two loopfuls of cell mass of LL-C31037 cultured on ATCC agar medium #172. Sufficient inoculum from the agar culture was used to provide a turbid seed after 72 hours of growth. The primary seed tube was incubated for 72 hours at 28° C., at 200 rpm using a gyro-rotary shaker with a 2-inch orbit. The primary seed (7 ml) was then used to inoculate a 250 ml Erlenmeyer flask containing 30 ml of seed medium. This secondary seed flask was incubated for 24 hours at 28° C., 200 rpm using a gyro-rotary shaker (2-inch orbit).

A fermentation production medium of the following formulation was prepared by combining: dextrose (added after autoclaving), 1%; maltrin M180, 6%; soyflour, 1%; yeast extract, 0.6%; Gamaco ($CaCO_3$), 0.1%; pH at 7.0.

One ml of secondary seed culture was inoculated into 50 ml of fermentation production medium in 250 ml Erlenmeyer flasks. These production flasks were incubated for 7 days at 26° C., 200 rpm using a gyro-rotary shaker (2-inch orbit).

B. Fermentor Fermentation

A seed medium of the following formulation was prepared by combining: dextrose (added after autoclaving), 2%; soluble starch, 2%; yeast extract (Difco), 0.3%; wheat hydrolysate WGE80M(DMV International), 0.5%; soy hydrolysate SE50MAF (DMV International), 1.5%; pH at 6.8 to 7.0.

One ml of frozen seed culture was inoculated into 1 liter of seed medium in a 4 liter Erlenmeyer flask. This seed flask was incubated for 72 hours at 30° C. at 250 rpm using a gyro-rotary shaker (2-inch orbit).

A fermentation production medium of the following formulation was prepared by combining: dextrose (added after autoclaving), 2%; maltrin M500, 8%; nutrisoy (GPC), 1%; yeast extract (Difco), 0.6%; Gamaco ($CaCO_3$), 0.1%; Macol P2000, 0.2%; pH at 6.8 to 7.0.

The 1 liter of seed culture was inoculated into 60 liters of fermentation production medium in a 70 liter fermentor. The fermentation was incubated for 5 days at 26° C., agitation at 350–550 rpm, aeration at 0.5 - 0.75 volvol$^{-1}$min$^{-1}$(VVM).

EXAMPLE 2

Purification of Compound (I) from LL-C31037

The cells from 8 L of a fermentation of culture LL-C31037 prepared in Example 1 were pelleted by centrifugation and extracted with 3×3 L of ethyl acetate. The extract was concentrated in vacuo and resuspended in a minimum volume of methanol. The solution was loaded onto C18 reverse phase silica (Bondesil C18 40μ) and eluted with 20%- 100% methanol in water. The fractions eluting from 60% methanol to 100% methanol were concentrated in vacuo. The prolylmeridamycin containing fractions were then chromatographed by preparative HPLC (YMC ODS-A 50×250 mm 10 u column, A: water B: methanol, gradient: 50% B to 80% B in 20 minutes, then hold at 80% methanol for 10 minutes, 20 ml/min). The compound of formula I was identified through LCMS analysis of fractions ($t_R$=22 min). These fractions were pooled to yield 30 mg crude prolylmeridamycin and further purified by preparative HPLC (YMC ODS-A 10×250 mm 10 μA: water B: acetonitrile, 2ml/min, gradient: 40% B to 60% B in 10 minutes, hold for 10 minutes, then to 70% B in 10 minutes). Fractions found to contain the compound of formula I ($t_R$=18 min) by LCMS analysis were pooled, and concentrated in vacuo to yield pure prolylmeridamycin (14.8 mg, 1.85 mg/L recovery).

EXAMPLE 3

Fermentation Conditions for Actinomycete Strain BD240

Fermentation conditions for cultivation under controlled conditions of an actinomycete strain designated BD240 produce a neuroprotective and neuroregenerative compound of formula (I) in the growth media.

The actinomycete strain is maintained in the culture collection of Wyeth Research, Pearl River, N.Y. 10965, as culture BD240. A viable culture of this microorganism has been deposited under the Budapest Treaty with the Patent Culture Collection, Northern Regional Research Laboratory (NRRL), U.S. Department of Agriculture, Peoria, Ill. 61604, and added to its permanent collection. Culture BD240 has been assigned the NRRL accession number 30810, deposited on Jan. 19, 2005.

Culture of actinomycete strain BD240 on agar plates, e.g., ATCC agar medium No. 174, produces no aerial mycelium. The substrate mycelium is tan and no soluble pigment is produced. The 16S rDNA sequence was determined for strain BD240 following isolation and direct sequencing of the amplified gene. The nucleotide sequence was aligned with the sequences of previously studied streptomycetes, and phylogenetic trees were generated by using two neighbor-joining tree algorithms. The 16S rDNA sequence supported classification of the strain in the genus *Streptomyces*.

Fermentation conditions to culture *Streptomyces* species BD240 for production of compound (I) were performed in flasks. Alternatively, production of higher volumes was performed in fermentors under similar conditions.

A. Flask Fermentation

A seed medium of the following formulation was prepared by combining: dextrose (added after autoclaving), 1%; soluble starch, 2%; yeast extract (Difco), 0.3%; wheat hydrolysate WGE80M(DMV International), 0.5%; soy hydrolysate SESOMAF (DMV International), 1.5%; pH at 6.8 to 7.0.

Ten ml of seed medium in a 25×150 mm glass tube was inoculated with 0.2 mL of a frozen seed culture of BD240. The seed tube was incubated for 48 hours at 30° C., at 200 rpm using a gyro-rotary shaker with a 2-inch orbit.

A fermentation production medium of the following formulation was prepared by combining: dextrose (added after autoclaving), 1%; maltrin M180, 6%; soyflour, 1%; yeast extract, 0.6%; Gamaco (CaCO$_3$), 0.1%; L-proline, 0.4%; 3-(N-morpholino)propanesulfonic acid, 20.9 g/L; pH at 7.0.

Seed culture (0.5 mL) was inoculated into 25 ml of fermentation production medium in 250 ml Erlenmeyer flasks. These production flasks were incubated for 5 days at 26° C., 250 rpm using a gyro-rotary shaker (2-inch orbit).

B. Fermentor Fermentation

A seed medium of the following formulation was prepared by combining: dextrose (added after autoclaving), 1%; soluble starch, 2%; yeast extract (Difco), 0.3%; wheat hydrolysate (WGE80M, DMV International), 0.5%; soy hydrolysate SE50MAF (DMV International), 1.5%; pH at 6.8 to 7.0.

Frozen seed culture (0.5 mL) was inoculated into 250 mL of seed medium in a 2 liter Erlenmeyer flask. This seed flask was incubated for 48 hours at 30° C. at 200 rpm using a gyro-rotary shaker (2-inch orbit).

A fermentation production medium of the following formulation was prepared by combining: dextrose (added after autoclaving), 1%; maltrin M180, 6%; soyflour, 1%; yeast extract (Difco), 0.6%; Gamaco (CaCO$_3$), 0.1%; L-proline, 0.4%; Macol P2000, 0.1%; pH at 6.8 to 7.0.

The 250 mL of seed culture was inoculated into 8 liters of fermentation production medium in a 10 liter fermentor. The fermentation was incubated for 7 days at 26° C., agitation at 480–650 rpm, aeration at 1.0 volvol$^{-1}$min$^{-1}$(VVM).

EXAMPLE 4

Purification of Compound (I) from BD240

The cells from a 10 L culture of BD240 prepared in Example 3 were pelleted by centrifugation. 5% Diaion-HP20 resin in water was added to the supernatant, and this was stirred at room temperature overnight. The resin was washed with methanol and the filtrate collected. To the cell pellet, 80:20 ethyl acetate methanol was added. This was repeatedly shaken and centrifuged, and the supernatant collected. The cell supernatant and the broth methanol filtrate were combined and concentrated in vacuo.

The crude extract was adsorbed onto silica (32–63μ, 60 Å), and fractionated by vacuum liquid chromatography (VLC). The compound was eluted with 5% methanol in dichloromethane. This material was then concentrated in vacuo, adsorbed onto silica (32–63μ, 60 Å) and loaded onto a flash silica column (60 mm×250 mm). The compound was eluted with 2% methanol in dichloromethane. This material was then concentrated in vacuo and loaded onto a Sephadex LH-20 (60×400 mm, methanol). The column was initially washed with 300 ml methanol and 30 ml fractions were collected and monitored by LCMS. Early fractions which contained the compound of interest were collected and concentrated. This semi-pure material was chromatographed by preparative HPLC (YMC ODS-A 50×250 mm 10μ column, A: water B: methanol, gradient: 55% B to 70% B in 200 minutes, 30 ml/min). The compound of formula (I) was identified through LCMS analysis of fractions. These fractions of interest were pooled, concentrated in vacuo to afford pure compound of formula (I) ($t_R$=130 min, 138 mg).

EXAMPLE 5

Purification of Compound (II) from BD240

The cells from a 10 L culture of BD240 were pelleted by centrifugation. 5% Diaion-HP20 resin in water was added to the supernatant, and this was stirred at room temperature overnight. The HP20 resin was washed with methanol and the filtrate collected. To the cell pellet, 80:20 ethyl acetate methanol was added. This was repeatedly shaken and centrifuged, and the supernatant collected. The cell supernatant and the broth methanol filtrate were combined and concentrated in vacuo.

The crude extract was adsorbed onto silica (32–63 μ, 60 Å), and fractionated by VLC. The compound was eluted with 5% methanol in dichloromethane. This material was concentrated in vacuo, adsorbed onto silica (32–63 μ, 60 Å) and loaded onto a flash silica column (60 mm×250 mm). The compound was eluted with 2% methanol in dichloromethane. This material was concentrated in vacuo and loaded onto Sephadex LH-20 (60×400 mm, methanol). The column was initially washed with 300 ml methanol and 30 ml fractions were collected and monitored by LCMS. Early fractions which contained the compound of interest were collected and concentrated. This semi-pure material was chromatographed by preparative HPLC (YMC ODS-A 50×250 mm 10μ column, A: water B: methanol, gradient: 55% B to 70% B in 200 minutes, 30 ml/min). Compound II was identified through LCMS analysis of fractions. These fractions of interest were pooled, concentrated in vacuo to afford pure compound II ($t_R$=150 min, 220 mg).

Compound II can be purified from actinomycete strain LL-C31037 using similar methods.

EXAMPLE 6

Neuroprotective Properties of Compound (I) in Neuronal Cell Culture

Mesencephalic dopaminergic neuron cultures were prepared as previously described in Pong et al., *J Neurochem.* 69: 986–994 (1997). Embryonic day 15 (E15) rat fetuses were collected and dissected in ice-cold phosphate-buffered saline (PBS). The ventral piece of tissue compromising the mesencephalic dopaminergic region was dissected out. Dissected pieces of tissue were pooled together and transferred to an enzymatic dissociation medium containing 20 IU/ml papain in Earle's balanced salt solution (Worthington Biochemical, Freehold, N.J., U.S.A.) and incubated for 60 minutes at 37° C. After enzymatic dissociation, the papain solution was aspirated and the tissue mechanically triturated with a fire-polished glass Pasteur pipette in complete medium [equal volumes of minimum essential medium (MEM) and F-12 nutrient mixture (Gibco BRL) supplemented with 0.1 mg/ml apotransferrin and 2.5 μg/ml insulin] containing 2,000 IU/ml DNase and 10 mg/ml ovomucoid protease inhibitor.

A. High-affinity Dopamine Uptake Assay

For dopamine uptake experiments, single-cell suspensions in complete media were seeded on poly-L-ornithine and laminin coated 24-well plates. The cultures were maintained for seven days prior to experimentation. Cultures were pretreated with various concentrations of the compound of formula (I) (washed with PBS and diluted with media to concentrations of 1 nM to 1000 nM) for 24 hours, then exposed to 10 μM the neurotoxin 1-methyl-4-phenylpyridinium (MPP$^+$) for 1 hour to assess the neuroprotective effect of the compound of formula (I) in cell culture. Following the 1 hour incubation, media was exchanged three times and fresh compound was added for an additional 48 hours.

More particularly, after 48 hours growth of mesencephalic dopaminergic neuron cultures following MPP$^+$ exposure, high-affinity $^3$H-dopamine uptake was performed using a modified method described by Prochiantz et al., *Nature* 293: 570–572 (1981). Cultures were washed with pre-warmed phosphate-buffered saline (PBS) containing 5.6 mM glucose and 1 mM ascorbic acid. Cultures were then incubated for 15 minutes at 37° C. with 50 nM $^3$H-dopamine (31 Ci/mmol, Du Pont-NEN, Wilmington, Del., U.S.A.). The cultures were washed twice with buffer and lysed with 0.5 N NaOH. The lysate was transferred to a scintillation vial containing Ultima Gold scintillation cocktail and radioactivity was determined with a liquid scintillation counter. Alternatively, culture lysates can be washed twice with buffer, incubated for 2 hours at room temperature with Optiphase Supermix scintillation cocktail (Wallac Scintillation Products, Gaithersburg, Md., USA), and radioactivity measured with a liquid scintillation counter.

TABLE 1

$^3$H-DOPAMINE UPTAKE (% UNTREATED CONTROL) IN CULTURED DOPAMINERGIC NEURONS AFTER MPP+ INDUCED TOXICITY

| TREATMENT | $^3$H-DOPAMINE UPTAKE (% UNTREATED CONTROL) |
| --- | --- |
| Untreated control | 100% |
| 10 μM MPP$^+$ | 40% |
| 1 nM Compound (I) | 45% |
| 10 nM Compound (I) | 52% |
| 100 nM Compound (I) | 61% |
| 1000 nM Compound (I) | 72% |

As shown in Table 1, the compound of formula (I), prolylmeridamycin, was neuroprotective against MPP$^+$-induced neurotoxicity in cultured dopaminergic neurons, with an EC$_{50}$ of 110 nM relative to a maximum protection (84% uptake) afforded by 10 ng/mL glial cell line-derived neurotrophic factor (GDNF). A similar study with meridamycin revealed that prolylmeridamycin is more potent in this assay than the meridamycin.

EXAMPLE 7

Neuroregenerative Properties of Compound (I) in Neuronal Cell Culture

Dissociated cortical neuron cultures were prepared as previously described [Pong et al., Exp Neurol. 2001 September; 171(1):84–97 (2001)]. Briefly, embryonic day 15 rat fetuses were collected and dissected in ice-cold PBS. Dissected cortices were pooled together and transferred to an enzymatic dissociation medium containing papain. After 30 min, the tissue was mechanically triturated with a fire-polished glass Pasteur pipette. Single-cell suspensions in complete media were seeded on poly-L-ornithine and laminin coated 96-well plates. 24 hours later, cultures were treated with various concentrations of compound of formula (I) for 72 hours. The cultures were then fixed and stained with a neurofilament primary antibody and a peroxidase-tagged secondary antibody. A peroxidase substrate (K-Blue Max) was added and the colorimetric change was measure on a colorimetric plate reader.

TABLE 2

NEUROFILAMENT CONTENT (FOLD-INCREASE
ABOVE UNTREATED CONTROL) IN CULTURED
CORTICAL NEURONS

| TREATMENT | NEUROFILAMENT CONTENT (FOLD-INCREASE ABOVE UNTREATED CONTROL) |
|---|---|
| Untreated control | 1.0 |
| 10 nM Compound (I) | 1.54 |
| 100 nM Compound (I) | 2.22 |
| 1 μM Compound (I) | 2.34 |
| 10 μM Compound (I) | 2.26 |

As shown in Table 2, addition of the compound to neuronal cells increased neuronal survival in cultured cortical neurons, with an $EC_{50}$ of 21 nM. A similar study with meridamycin revealed that prolylmeridamycin is more potent in this assay than the meridamycin.

EXAMPLE 8

Neuroregenerative Properties of Compound (I) in Cultured Cortical Neurons

Dissociated cortical neuron cultures were prepared as previously described (Pong et al., cited above, 2001). Briefly, embryonic day 15 rat fetuses were collected and dissected in ice-cold PBS. Dissected cortices were pooled together and transferred to an enzymatic dissociation medium containing papain. After 30 minutes, the tissue was mechanically triturated with a fire-polished glass Pasteur pipette. Single-cell suspensions in complete media were seeded on poly-L-ornithine and laminin coated 96-well plates. After 24 hours, cultures were treated with various concentrations of the compound of formula I for 72 hours. The cultures were then fixed and stained with an anti-tubulin primary antibody (TUJ-1) and a fluorescent-tagged secondary antibody. Neurite outgrowth was determined by using the Enhanced Neurite Outgrowth (ENO) algorithm with the Cellomics ArrayScan and expressed as total neurite length per cell.

TABLE 3

Total Neurite Length (% Above Control)
in Cultured Cortical Neurons

| Treatment | Total Neurite Length (% Above Control) |
|---|---|
| 10 nM Compound | 30% |
| 100 nM Compound | 51% |
| 1 mM Compound | 120% |
| 10 mM Compound | 178% |

EXAMPLE 9

Neuroregenerative Properties of Compound (I) in Cultured Dorsal Root Ganglia

Dissociated dorsal root ganglia cultures were prepared as previously described [A. Wood et al., "Stimulation of neurite outgrowth by immunophilin ligands: quantitative analysis by Cellomics Array scan" Society for Neuroscience (2004), abstract 104.3] Briefly, postnatal day 3–5 rat pups were euthanized. The spinal columns were removed and individual dorsal root ganglia (DRG) were dissected out. Dissected DRG were pooled together and transferred to an enzymatic dissociation medium containing papain. After 60 minutes, the tissue was mechanically triturated with a fire-polished glass Pasteur pipette. Single-cell suspensions in complete media were seeded on poly-L-ornithine and laminin coated 96-well plates. After 24 hours, cultures were treated with various concentrations of the compound of formula I for 72 hours. The cultures were then fixed and stained with an anti-tubulin primary antibody (TUJ-1) and a fluorescent-tagged secondary antibody. Neurite outgrowth was determined by using the Enhanced Neurite Outgrowth (ENO) algorithm with the Cellomics ArrayScan and expressed as total neurite length per cell.

TABLE 4

Total Neurite Length (% Above Control)
in Cultured Dorsal Root Ganglia

| Treatment | Total Neurite Length (% Above Control) |
|---|---|
| 10 nM Compound | 2% |
| 100 nM Compound | 7% |
| 1 mM Compound | 21% |
| 10 mM Compound | 44% |

When ranges are used herein for physical properties, such as molecular weight, or chemical properties, such as chemical formulae, all combinations and subcombinations of ranges and specific embodiments therein are intended to be included. All publications cited in this specification, and the deposits, are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A compound of formula (I) or a pharmaceutically acceptable salt thereof:

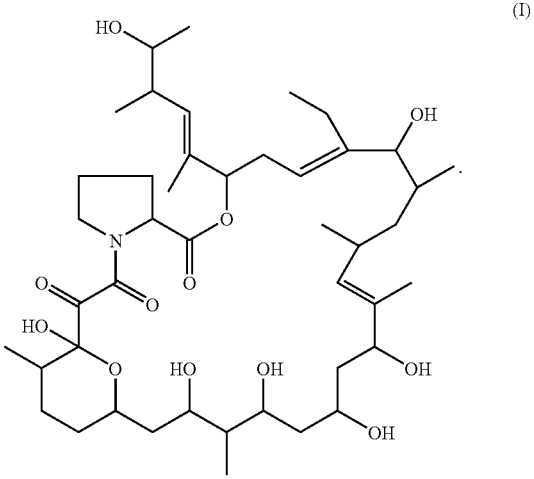

(I)

2. The compound according to claim 1 having the proton magnetic resonance spectrum shown in FIG. 1.

3. A composition comprising a compound according to claim 1 and one or more pharmaceutically acceptable carriers, excipients, or diluents.

* * * * *